(12) United States Patent
Stellon et al.

(10) Patent No.: US 8,968,189 B2
(45) Date of Patent: Mar. 3, 2015

(54) FLEXIBLE ACCESS ASSEMBLY WITH MULTIPLE PORTS

(75) Inventors: Gene A. Stellon, Burlington, CT (US); Elias Hartoumbekis, New Haven, CT (US)

(73) Assignee: Covidien LP, Mansfield, MA (US)

( * ) Notice: Subject to any disclaimer, the term of this patent is extended or adjusted under 35 U.S.C. 154(b) by 668 days.

(21) Appl. No.: 12/754,638

(22) Filed: Apr. 6, 2010

(65) Prior Publication Data

US 2010/0286484 A1 Nov. 11, 2010

Related U.S. Application Data

(60) Provisional application No. 61/176,216, filed on May 7, 2009.

(51) Int. Cl.
A61B 1/32 (2006.01)
A61B 17/34 (2006.01)

(52) U.S. Cl.
CPC .......... *A61B 17/3423* (2013.01); *A61B 17/3462* (2013.01); *A61B 2017/3429* (2013.01); *A61B 2017/3445* (2013.01); *A61B 2017/3466* (2013.01)
USPC ....................................................... 600/206

(58) Field of Classification Search
USPC .................................... 602/63; 600/208, 206
See application file for complete search history.

(56) References Cited

U.S. PATENT DOCUMENTS

| | | | |
|---|---|---|---|
| 5,073,169 A | 12/1991 | Raiken | |
| 5,183,471 A | 2/1993 | Wilk | |
| 5,375,588 A | 12/1994 | Yoon | |
| 5,480,410 A * | 1/1996 | Cuschieri et al. | 606/213 |
| 5,672,168 A | 9/1997 | de la Torre et al. | |
| 5,842,971 A | 12/1998 | Yoon | |
| 5,906,577 A * | 5/1999 | Beane et al. | 600/207 |
| 5,957,913 A | 9/1999 | de la Torre et al. | |
| 6,024,736 A | 2/2000 | de la Torre et al. | |
| 6,086,603 A | 7/2000 | Termin et al. | |
| 6,217,555 B1 | 4/2001 | Hart et al. | |
| 6,454,783 B1 | 9/2002 | Piskun | |
| 6,488,692 B1 | 12/2002 | Spence et al. | |
| 6,551,270 B1 | 4/2003 | Bimbo et al. | |
| 7,008,377 B2 | 3/2006 | Beane et al. | |
| 7,101,353 B2 | 9/2006 | Lui et al. | |
| 7,217,277 B2 | 5/2007 | Parihar et al. | |

(Continued)

FOREIGN PATENT DOCUMENTS

| | | |
|---|---|---|
| EP | 1 774 918 A1 | 4/2007 |
| WO | WO 97/33520 | 9/1997 |

(Continued)

OTHER PUBLICATIONS

European Search Report for EP 10 25 0885 date of completion is Aug. 18, 2010 (3 pages).

*Primary Examiner* — David Bates

(57) ABSTRACT

An access assembly configured to receive one or more surgical instruments is provided. The access assembly includes a flexible housing having a proximal end and a distal end, the housing defining a longitudinal passageway extending from the proximal end to the distal end and a seal assembly received within the longitudinal passageway of the housing. The seal assembly defining a plurality of ports each configured to receive an instrument inserted therethrough in a sealing manner.

19 Claims, 6 Drawing Sheets

(56) References Cited

U.S. PATENT DOCUMENTS

| | | | |
|---|---|---|---|
| 7,276,075 B1 | 10/2007 | Callas et al. | |
| 7,297,106 B2 * | 11/2007 | Yamada et al. | 600/208 |
| 7,736,306 B2 * | 6/2010 | Brustad et al. | 600/208 |
| 7,766,824 B2 * | 8/2010 | Jensen et al. | 600/208 |
| 7,798,898 B2 | 9/2010 | Luciano, Jr. et al. | |
| 7,850,600 B1 * | 12/2010 | Piskun | 600/114 |
| 8,137,267 B2 * | 3/2012 | Shelton et al. | 600/203 |
| 8,187,178 B2 * | 5/2012 | Bonadio et al. | 600/208 |
| 8,425,410 B2 * | 4/2013 | Murray et al. | 600/203 |
| 8,485,970 B2 * | 7/2013 | Widenhouse et al. | 600/201 |
| 8,550,992 B2 * | 10/2013 | Kleyman | 600/208 |
| 8,574,153 B2 * | 11/2013 | Richard | 600/206 |
| 8,795,289 B2 * | 8/2014 | Fowler et al. | 606/108 |
| 2004/0167543 A1 | 8/2004 | Mazzocchi et al. | |
| 2005/0096695 A1 | 5/2005 | Olich | |
| 2006/0020241 A1 | 1/2006 | Piskun et al. | |
| 2006/0247498 A1 * | 11/2006 | Bonadio et al. | 600/208 |
| 2006/0247499 A1 | 11/2006 | Butler et al. | |
| 2006/0247516 A1 | 11/2006 | Hess et al. | |
| 2008/0255519 A1 | 10/2008 | Piskun et al. | |
| 2009/0036745 A1 * | 2/2009 | Bonadio et al. | 600/208 |
| 2009/0093752 A1 | 4/2009 | Richard et al. | |
| 2009/0221966 A1 * | 9/2009 | Richard | 604/164.04 |
| 2009/0326332 A1 | 12/2009 | Carter | |
| 2010/0249526 A1 * | 9/2010 | Shelton et al. | 600/208 |

FOREIGN PATENT DOCUMENTS

| | | |
|---|---|---|
| WO | WO 01/49363 A1 | 7/2001 |
| WO | WO 2008/093313 A1 | 8/2008 |

* cited by examiner

FLEXIBLE ACCESS ASSEMBLY WITH MULTIPLE PORTS

CROSS REFERENCE TO RELATED APPLICATION

The present application claims the benefit of and priority to U.S. Provisional Application Ser. No. 61/176,216 filed on May 7, 2009, the entire contents of which are incorporated herein by reference.

BACKGROUND

1. Technical Field

The present disclosure relates to a flexible access assembly for use in single incision surgical procedures. More particularly, the present disclosure relates to a flexible access assembly having multiple instrument ports.

2. Background of Related Art

Methods and apparatus for performing closed surgical procedures are known. Such procedures greatly reduce postoperative recovery time and minimize scarring to the patient. These procedures typically involve inserting one or more access assemblies through the abdominal wall of the patient and insufflating the abdominal cavity. A laparoscope or other viewing instrument is inserted through one of the access assemblies, or directly through the abdominal wall, to provide the clinician with an image of the abdominal cavity. The surgeon is then able to perform the procedure within the abdominal cavity by manipulating instruments that have been extended through the access assemblies.

The number and type of instruments that a surgeon may use to complete a closed procedure is limited by the number, size and configuration of the access assemblies that have been inserted into the abdominal cavity. Because traditional access assemblies are configured to provide access for only a single instrument, the simultaneous use of any additional instruments requires a corresponding access assembly. For each additional access assembly necessary to complete the procedure, an additional incision must be created. Each additional incision increases the length of the procedure and may prolong post-operative recovery time.

Therefore, it is desirable to provide an access assembly for insertion through a single incision in the body of a patient which provides multiple ports for receipt of one or more surgical instruments.

SUMMARY

Accordingly, an access assembly configured to receive one or more surgical instruments is provided. The access assembly includes a flexible housing having a proximal end and a distal end, the housing defining a longitudinal passageway extending from the proximal end to the distal end and a seal assembly received within the longitudinal passageway of the housing. The seal assembly defining a plurality of ports each configured to receive an instrument inserted therethrough in a sealing manner.

The housing of the access assembly may include a central portion and an upper rim at a proximal end of the central portion and a lower rim at a distal end of the central portion. The upper rim may have a diameter greater than a diameter of the central portion. The housing may include a groove formed in an inner surface of the housing for receipt of the seal assembly. The groove may be formed near a proximal end of the housing. Alternatively, the seal assembly may be integrally formed with the housing. The seal assembly may include a circular disk. In one embodiment, the housing may be configured to be received through an incision in a sealing manner. Each of the plurality of ports may include a seal configured to seal the ports in the absence of an instrument being inserted therethrough. The port may include a zero-closure or duck-bill seal. The seal assembly may be formed of a flexible material. The seal assembly may include a first and second layer.

Also provided is a method of accessing a body cavity. The method including the steps of creating an incision through the abdominal wall, providing an access assembly having a flexible housing and including a seal assembly having one or more ports, compressing the flexible housing such that it may be inserted through the incision, inserting the compressed housing through the incision, releasing the compressed housing to permit the housing to return to an original shape, and receiving the seal assembly within the housing.

The method may further include the steps of receiving one or more instruments through the one or more ports of the seal assembly and removing the seal assembly. The method may further include the step of receiving a second seal assembly within the housing. The housing may be configured to be received within the incision in a sealing manner.

DESCRIPTION OF THE DRAWINGS

Embodiments of the access assembly are disclosed herein with reference to the drawings, wherein.

DETAILED DESCRIPTION

An embodiment of the presently disclosed access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
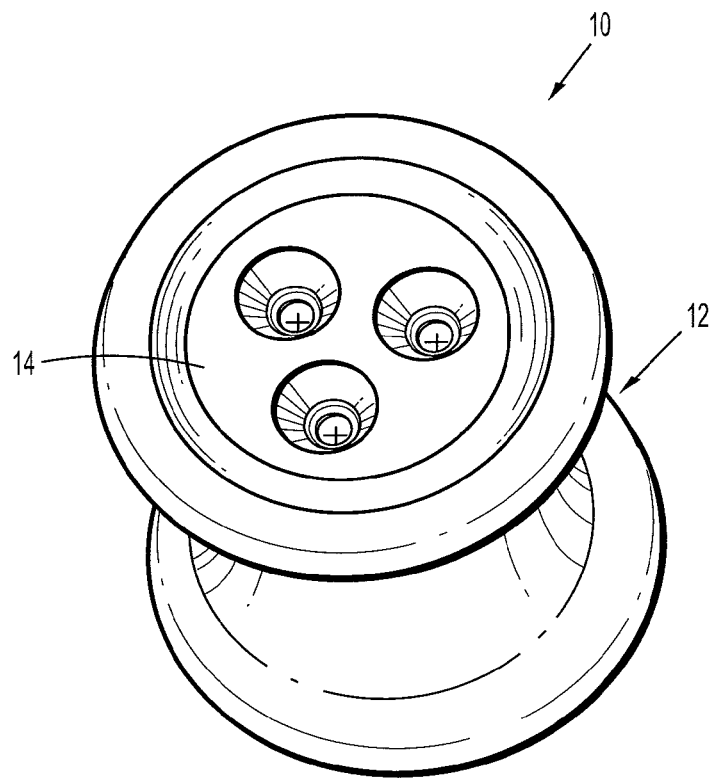
FIG. 1 is a perspective view of an embodiment of an access assembly according to the aspects of the present disclosure.
Figures 2, 3:
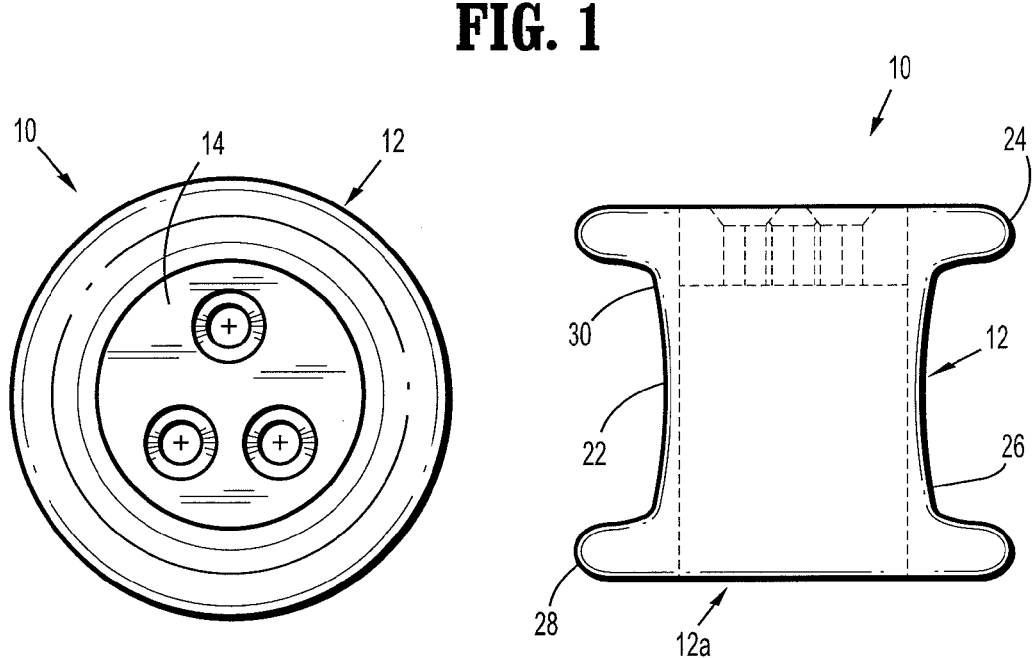
FIG. 2 is a top view of the access assembly of FIG. 1.
FIG. 3 is a side view of the access assembly of FIG. 1 with a seal assembly shown in phantom.

Referring to FIGS. 1-3, there is disclosed an access assembly 10 for use in single incision surgery. Access assembly 10 is flexible or compressible to allow it to be inserted through a single incision in the body of a patient such that after insertion it will expand and seal within the incision. Additionally, the flexible nature of access assembly 10 allows surgical instruments inserted therethrough to be manipulated about their axes and thus allow a higher degree of movement of the surgical instruments to orient them relative to the tissue being operated upon.

Still referring to FIGS. 1-3, access assembly 10 includes an outer flexible housing 12 and an inner seal assembly 14 supported within housing 12. Housing 12 defines a longitudinal passageway 12a (FIG. 6) extending therethrough. Housing 12 may be formed of various materials such as, for example, silicone, thermoplastic elastomers (TPE), rubber, foam, gel, etc. In this manner, housing 12 of access assembly 10 may be compressed or squeezed and inserted through an incision in the body of a patient. In one embodiment, housing 12 includes TPE material that is infused with an inert gas, e.g. $CO_2$ or Nitrogen, to form a foam structure. Housing 12 may be coated with a lubricant, e.g. Parylene N or C, in order to create a lubricious surface finish on all external surface. Various other coatings, e.g., hydrophilic, hydrophobic, bio-agents, anti-infection, analgesic, may also be employed. The coating facilitates insertion of housing 12 into an incision.

Figure 6:
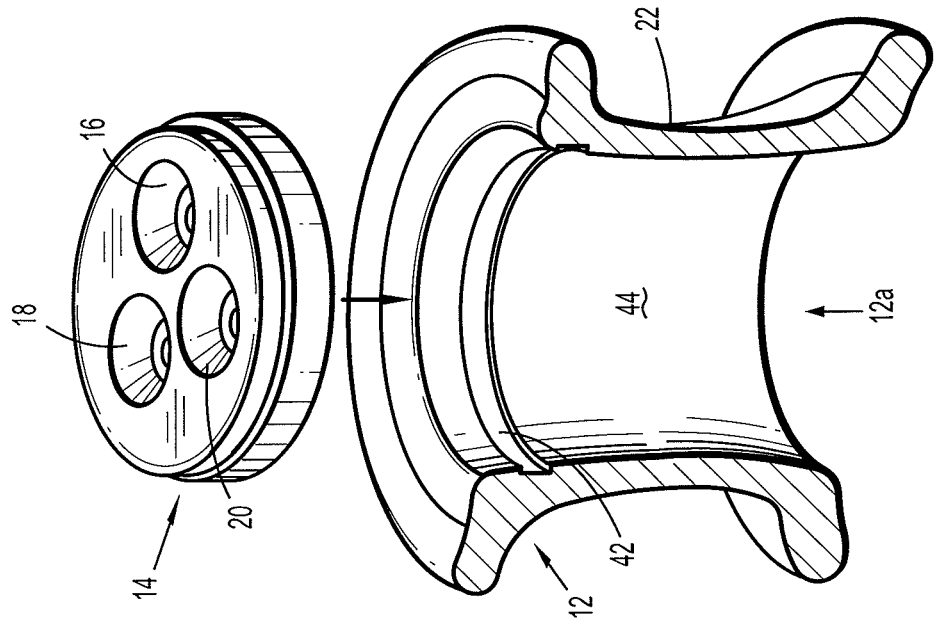
FIG. 6 is a partial cross-sectional perspective view of the access assembly of FIGS. 1-5 with parts separated.

Turning to FIGS. 3 and 6, housing 12 includes a central portion 22 having an upper rim 24 located at a proximal end 26 of central portion 22 and a lower rim 28 located at a distal end 30 of central portion 22. Upper rim 24 and lower rim 28 aid in preventing movement of access assembly 10 longitudinally through incision "I" (FIG. 7) in the patient. A groove 42 is formed about an inner surface 44 of housing 12. Although shown formed near a proximal end of housing 12, it is envisioned that groove 42 may be formed along any portion of inner surface 44.

Figure 1A:
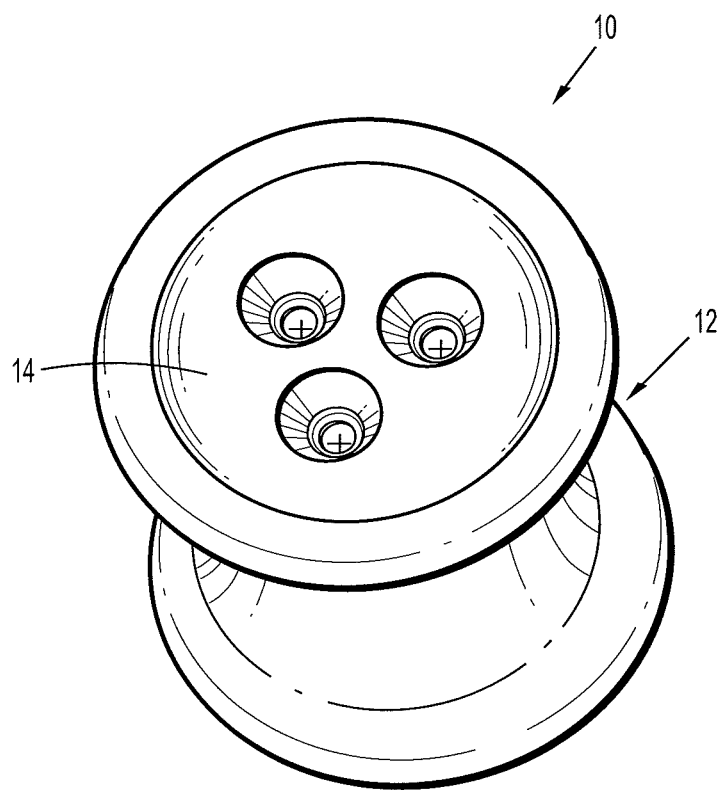
FIG. 1A is a perspective view of an alternate embodiment of an access assembly according to the aspects of the present disclosure.
Figure 4:
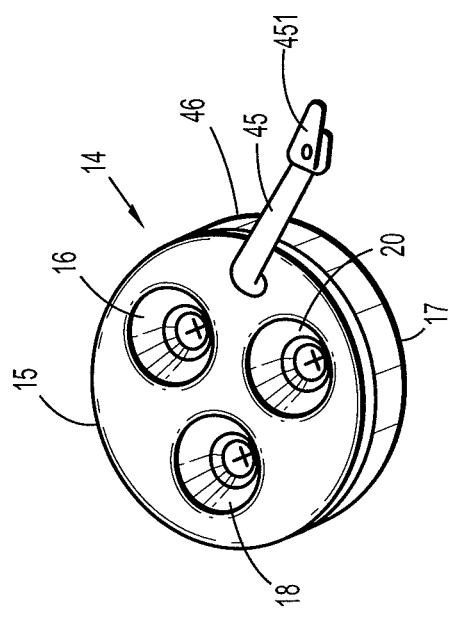
FIG. 4 is a perspective view of the seal assembly of FIGS. 1-3.
Figure 5:
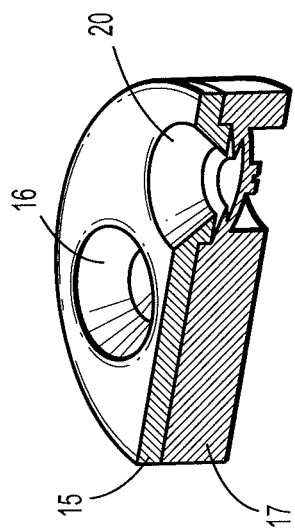
FIG. 5 is a cross-section perspective view of the seal assembly of FIGS. 1-4.

With particular reference now to FIGS. 4-6, seal assembly 14 is configured to be received within housing 12. Seal assembly 14 may be integrally formed with housing 12 (FIG. 1A), or instead may be provided as a separate component, as shown. When provided as a separate component, seal assembly 14 is configured to be received within groove 42 formed in inner surface 44 of housing 12. Upon assembly, a circumferential edge 46 of seal assembly 14 fits within groove 42 in friction fit fashion such that circumferential edge 46 forms a fluid tight seal within groove 42. It should be recognized that the seal assembly 14, and/or the portion of the housing 12 into which it fits or is part of, may be any one of a variety of shapes, e.g., circular, oval-shaped, square, rectangular, or any suitable shape.

Seal assembly 14 includes a plurality of ports 16, 18, 20. As shown, seal assembly 14 includes three ports, however, seal assembly 14 may include any number of ports or openings. Ports 16, 18, 20 are provided to receive surgical instruments of various types and sizes through seal assembly 14. In one embodiment, ports 16, 18, 20 are configured to receive 5 mm or smaller instruments in a sealing manner. It is envisioned that seal assemblies of various configurations may be interchanged with housing 12 during the course of a procedure to facilitate insertion of different instruments through access assembly 10.

With reference still to FIGS. 4 and 5, seal assembly 14 includes first and second sealing layers 15, 17. First and second sealing layers 15, 17 define seal ports 16, 18 and 20. First and second sealing layers 15, 17 may be formed of the same material, or instead, of different material. In one embodiment, first sealing layer 15 is formed from a semi-rigid plastic, while second sealing layer 17 is formed of a foam material. First and second layers 15, 17 may be integrally formed with one another, or instead, may be securely affixed to the other using adhesive, mechanical fasteners or other suitable methods. First and second sealing layers 15, 17 are configured such that seal ports 16, 18, 20 are closed or sealed when access assembly 10 is not in use. First and second sealing layers 15, 17 are further configured to form a seal about instruments of various diameters as the instruments are selectively received through seal ports 16, 18, 20. For example, one or both of first and second sealing layers 15, 17 may form a slot, duck-bill or zero-closure seal. FIG. 4 shows an embodiment of the present invention, in which the device includes an insufflation/smoke evacuation connection 45 including a valve 451, e.g., a stopcock valve. It should be recognized that, in such embodiments where an insufflation/smoke evacuation connection 45 is included, such connection may be in any suitable configuration.

Referring now to FIGS. 7-10, the use of access assembly 10 in a single incision surgical procedure will now be described. Although access assembly 10 will be described as relates to relates to a procedure for excising and removing a body organ, the aspects of the present disclosure may be modified for use in any closed procedure and should not be read as limited to the procedure herein described.

Figure 7:
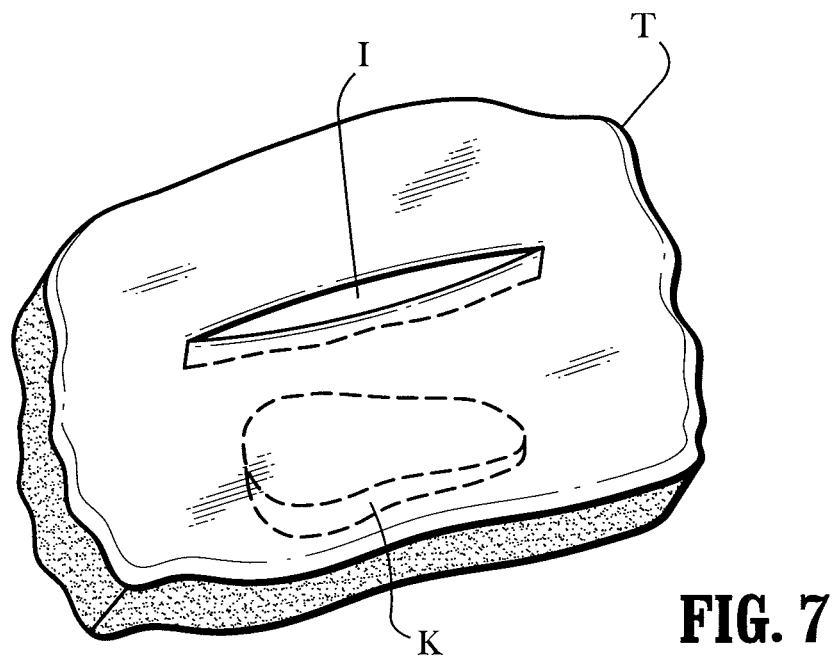
FIG. 7 is a perspective view of a tissue section having an incision therethrough with an underlying body organ shown in phantom.
Figure 8:
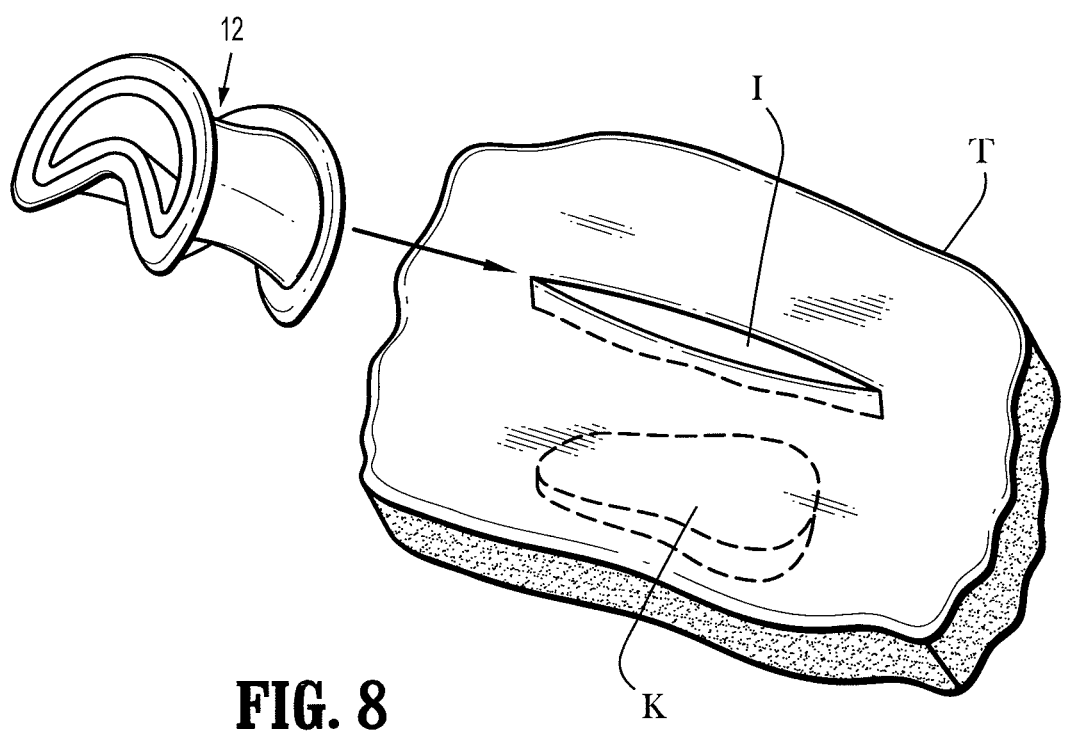
FIG. 8 is a perspective view of the access assembly of FIG. 1 prepared for insertion through the incision in the tissue.

Referring initially to FIG. 7, a single incision "I" is formed through a body tissue "T" and above a body organ, such as, for example, kidney "K". Turning now to FIG. 8, once incision "I" has been formed through body tissue "T", housing 12 of access assembly 10 may be squeezed or compressed to reduce housing 12 to a relatively smaller diameter for insertion through incision "I". As noted hereinabove, housing 12 is formed of a flexible material which allows access assembly 10 to be compressed. It should be recognized that the housing 12 may be compressed into any suitable configuration prior to being inserted into an incision, not merely the configuration shown in FIG. 8. For example, in an embodiment, prior to insertion the housing 12 is clamped at its distal end while the proximal end of the housing 12 remains essentially uncompressed, and the clamped distal end is inserted into the incision.

Figure 9:
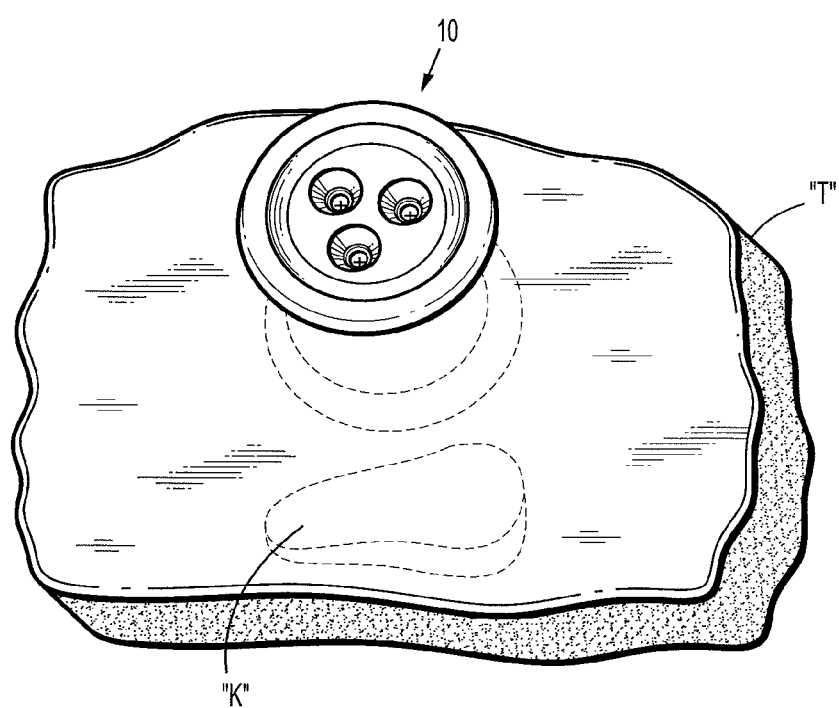
FIG. 9 is a perspective view of the flexible access assembly of FIG. 1 positioned through the incision in the tissue.

Referring to FIG. 9, once flexible access assembly 10 has been inserted through incision "I" pressure on the housing 12 may be released allowing housing 12 to return towards its initial uncompressed state within incision "I". Typically, the incision "I" is formed having a size that is smaller than the diameter of the initial uncompressed state of the housing 12. In this manner, when in place within the incision "I", the housing 12 contacts and presses against the inner surface of the incision "I", thereby retracting the opening and sealing with the incision "I". Since incisions are often slit-shaped when formed, the portion of the housing 12 that is located within the incision may be somewhat oval-shaped (when viewed from above). As noted hereinabove, housing 12 includes upper rim 24 and lower rim 28 to prevent migration of access assembly 10 through incision "I" in body tissue "T". At this time, if seal assembly 14 is not integrally formed with housing 12, seal assembly 14 is received within groove 42 of housing 12. As noted above, access assembly 10 may be configured such that seal assembly 14 may be replaced or exchanged during a procedure in the event of damage to the assembly or to provide alternatively configured ports.

Figure 10:
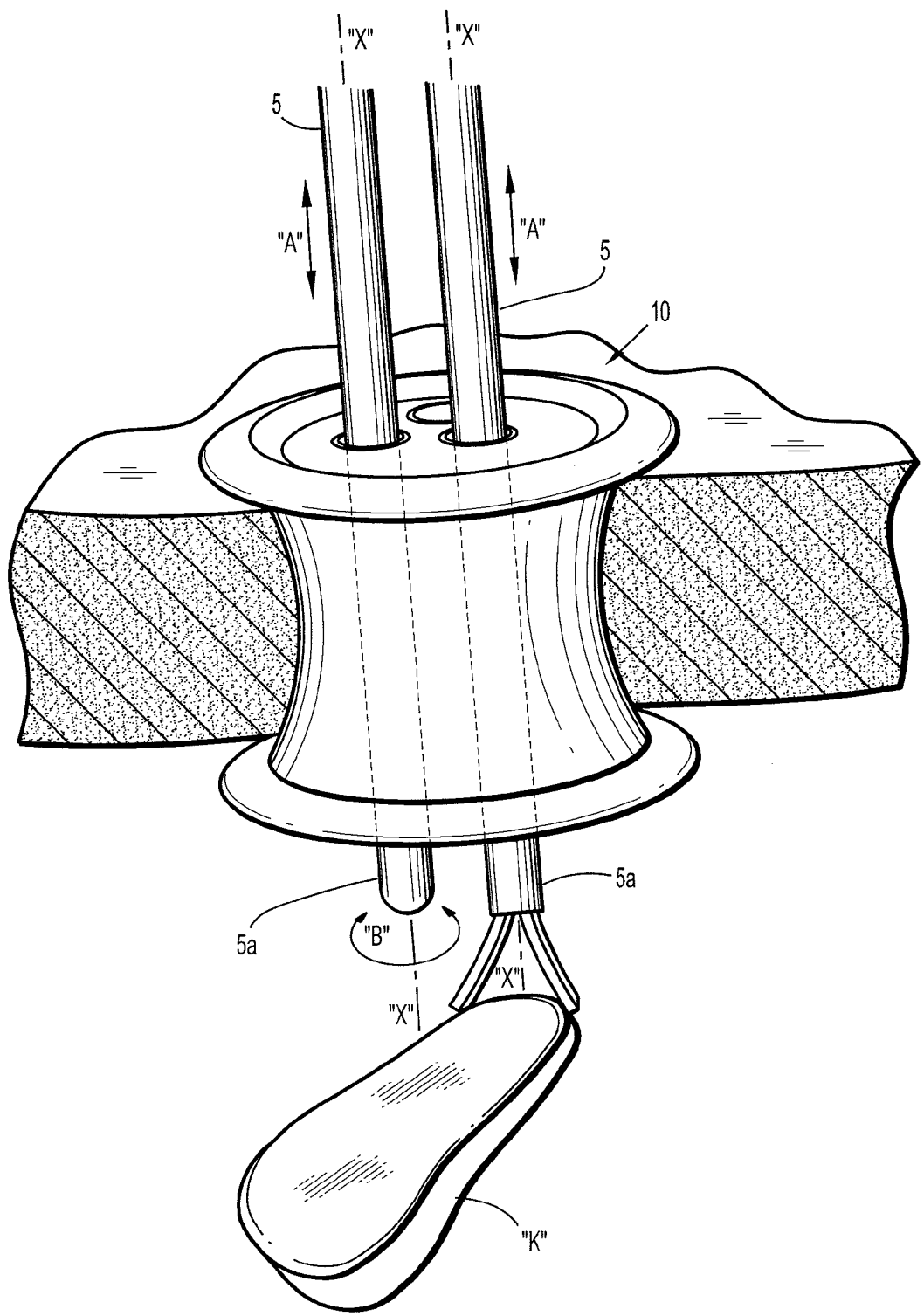
FIG. 10 is a side view, partially shown in section, of the access assembly of FIG. 1, with surgical instruments inserted therethrough and positioned above the body organ.

With reference now to FIG. 10, once the body cavity has been properly insufflated, kidney K may be operated upon to excise it from the surrounding tissue. The body cavity may be insufflated through one of seal ports 16, 18, 20. Surgical instrument 5, such as, for example, tissue graspers or surgical staplers may be inserted through any of seal ports 16, 18, 20. Seal ports 16, 18, 20 are configured to receive instrument 5 in a sealing manner. Instrument 5 is inserted and retracted through access assembly 10, in the direction of arrows "A", through any one of seal ports 16, 18, 20. Due to the flexible nature of access assembly 10, while received through access assembly 10, a distal end 5a of instrument 5 may be manipulated in any direction, as represented by arrows "B". This allows the surgeon to manipulate or orient distal end 5a of instrument 5 at various locations relative to the tissue being operated upon. Each instrument received through access assembly 10 may also be manipulated relative to each other such that a surgeon or surgeons may orient the instruments independent of each other. As discussed above, at any time during the procedure, seal assembly 14 may be interchanged with seal assemblies having alternative configurations, such that different types and/or numbers of instruments may be used to complete the procedure.

In one procedure, once kidney "K" has been excised or severed for harvesting, seal assembly 14 is removed from housing 12 such that kidney "K" may be removed through longitudinal passage 12a of housing 12. Once kidney K has been removed from the body, housing 12 is removed and incision "I" is closed in a conventional manner. Alternatively, once kidney K has been removed from the body, the seal assembly 14 may be re-positioned within the housing 12. In this manner, the surgical site may, if desired, be re-insufflated, allowing a surgeon to exam the surgical site to be sure that he or she is satisfied with the condition of the surgical site. Once satisfied, the housing 12 may then be removed and incision "I" may be closed in a conventional manner.

It will be understood that various modifications may be made to the embodiments disclosed herein. For example, as noted hereinabove, the disclosed flexible access assembly may be provided with multiple seal ports in excess of the disclosed three seal ports. Additionally, the diameters or configuration of the disclosed seal ports need not be identical but may be varied depending upon the contemplated surgical instruments to be utilized therethrough. Furthermore, while the seal assembly is shown as including a valve arrangement, any one or more of openings through the seal assembly may instead be open lumen into which cannulas may be inserted and maintained during a surgical procedure. Therefore, the above description should not be construed as limiting, but merely as exemplifications of particular embodiments. Those skilled in the art will envision other modifications within the scope and spirit of the claims appended hereto.

The invention claimed is:

1. An access assembly for insertion through an incision in tissue, the access assembly comprising:
    a unitary flexible housing having a proximal end configured to be placed against an outer surface of the tissue and a distal end configured to be passed through the incision and placed against an inner surface of the tissue, the housing defining a longitudinal passageway extending from the proximal end to the distal end and a groove formed in an inner surface of the longitudinal passageway of the housing; and
    a seal assembly configured to be positioned within the groove of the housing and defining a plurality of ports, wherein each port includes a zero closure seal that forms a fluid tight seal about a surgical instrument inserted therethrough and forms a fluid tight seal upon removal of the surgical instrument, the seal being maintained between the inner surface of the tissue and the outer surface of the tissue when the seal assembly is positioned within the groove, wherein an upper surface of the seal assembly is coplanar with an upper rim forming the proximal end of the housing when the seal assembly is positioned within the groove and each of the zero closure seals is positioned between the proximal end and the distal end of the housing when the seal assembly is positioned within the groove.

2. The access assembly as recited in claim 1, wherein the housing has a central portion, the upper rim being at a proximal end of the central portion.

3. The access assembly as recited in claim 2, wherein the housing has a lower rim at a distal end of the central portion.

4. The access assembly as recited in claim 2, wherein the upper rim has a diameter greater than a diameter of the central portion.

5. The access assembly as recited in claim 1, wherein the seal assembly includes a disk that is one of circular, oval-shaped, square and rectangular.

6. The access assembly as recited in claim 1, wherein the housing includes a coating that is at least one of parylene, hydrophilic, hydrophobic, bio-agents, anti-infection and analgesic.

7. The access assembly as recited in claim 1, wherein the seal assembly is formed of a flexible material.

8. The access assembly as recited in claim 1, wherein the seal assembly includes a first layer and a second layer.

9. The access assembly as recited in claim 1, wherein each port of the seal assembly is off-center of a central longitudinal axis through the seal assembly.

10. The access assembly of claim 1, wherein a circumferential edge of the seal assembly fits within the groove forming a fluid tight seal therewith.

11. The access assembly of claim 1, wherein a lower surface of the seal assembly is positioned between the proximal and distal ends of the housing.

12. The access assembly of claim 1, wherein the seal assembly in its entirety is positioned between the proximal and distal ends of the housing.

13. The access assembly of claim 1, wherein the plurality of ports are coplanar.

14. An access assembly for insertion through an incision in tissue, the access assembly comprising:
    a unitary flexible foam housing having a proximal end configured to be placed against an outer surface of the tissue and a distal end configured to be passed through the incision and placed against an inner surface of the tissue, the housing defining a longitudinal passageway extending from the proximal end to the distal end and a groove formed in an inner surface of the longitudinal passageway of the housing; and
    a seal assembly configured to be positioned within the groove, the seal assembly defining a plurality of ports and including a plurality of zero closure seals, each one of the plurality of zero closure seals associated with a corresponding one of the plurality of ports and forming a fluid tight seal about a surgical instrument inserted therethrough and forming a fluid tight seal in the absence of a surgical instrument, the seal being maintained between the inner surface of the tissue and the outer surface of the tissue when the seal assembly is positioned within the groove, wherein each of the plurality of zero closure seals is positioned between the proximal end and the distal end of the housing when the seal assembly is positioned within the groove.

15. The access assembly of claim 1, wherein the flexible housing is formed of foam.

16. The access assembly of claim 1, wherein the seal assembly includes a first layer and a second layer.

17. The access assembly of claim 16, wherein the first layer is formed of plastic and the second layer is formed of foam.

18. The access assembly of claim 1, wherein the seal assembly forms a fluid tight seal with the housing when the seal assembly is received within the groove in the housing.

19. The access assembly of claim 1, wherein the seal assembly includes a circular disk forming a friction fit with the housing when the seal assembly is received within the groove in the housing.

* * * * *